(12) United States Patent
Lockwood et al.

(10) Patent No.: US 9,283,364 B2
(45) Date of Patent: Mar. 15, 2016

(54) METHOD AND APPARATUS FOR AN APPLICATOR

(71) Applicant: Medline Industries, Inc., Mundelein, IL (US)

(72) Inventors: Robert Lockwood, Libertyville, IL (US); Andrew Nachenberg, Grayslake, IL (US); Derek Roberts, Chicago, IL (US)

(73) Assignee: Medline Industries, Inc., Mundelein, IL (US)

( * ) Notice: Subject to any disclaimer, the term of this patent is extended or adjusted under 35 U.S.C. 154(b) by 142 days.

(21) Appl. No.: 14/254,018

(22) Filed: Apr. 16, 2014

(65) Prior Publication Data

US 2015/0297876 A1 Oct. 22, 2015

(51) Int. Cl.
*B43K 5/14* (2006.01)
*A61F 13/40* (2006.01)

(52) U.S. Cl.
CPC .................................. *A61M 35/006* (2013.01)

(58) Field of Classification Search
CPC ........................ A61M 35/006; A61M 35/003
USPC ................................................ 401/132–134
See application file for complete search history.

(56) References Cited

U.S. PATENT DOCUMENTS

| | | | |
|---|---|---|---|
| 4,148,318 A | 4/1979 | Meyer | |
| 4,925,327 A | 5/1990 | Wirt | |
| 5,308,180 A | 5/1994 | Pournoor | |
| D351,229 S | 10/1994 | Wirt | |
| 5,658,084 A | 8/1997 | Wirt | |
| 5,690,958 A | 11/1997 | McGrath | |
| 5,791,801 A | 8/1998 | Miller | |
| 6,371,675 B1 | 4/2002 | Hoang | |
| D458,367 S | 6/2002 | Zaspel | |
| 6,422,778 B2 | 7/2002 | Baumann | |
| 6,533,484 B1 | 3/2003 | Osei | |
| D503,229 S | 3/2005 | Davis | |
| 6,945,722 B2 | 9/2005 | Colburn | |
| 6,991,394 B2 * | 1/2006 | Tufts | A45D 34/04 401/133 |
| 7,201,525 B2 | 4/2007 | Mohiuddin | |
| 7,306,390 B2 * | 12/2007 | Quintero | A61B 17/00491 401/132 |
| 7,377,710 B2 | 5/2008 | Baumann | |
| 7,540,681 B2 | 6/2009 | Cybulski | |
| 7,572,079 B2 * | 8/2009 | Wong | A46B 11/0041 222/83 |
| 7,824,122 B2 * | 11/2010 | Flores | A61M 35/006 401/133 |
| 7,946,779 B2 | 5/2011 | Kaufman | |
| 7,993,066 B2 | 8/2011 | Flores | |
| 8,118,766 B2 | 2/2012 | Davis | |
| 8,801,372 B2 * | 8/2014 | Shi | F01D 11/24 415/173.1 |
| 2010/0003066 A1 | 1/2010 | Thorpe | |
| 2012/0051829 A1 | 3/2012 | Margoosian | |

FOREIGN PATENT DOCUMENTS

| | | |
|---|---|---|
| WO | 02055147 A2 | 7/2002 |
| WO | 2007076121 A1 | 7/2007 |
| WO | 2009076612 A1 | 6/2009 |

* cited by examiner

*Primary Examiner* — Jennifer C Chiang
(74) *Attorney, Agent, or Firm* — Fitch, Even, Tabin & Flannery LLP

(57) ABSTRACT

An applicator includes a puncture protrusion disposed on an inner surface of an internal chamber of a handle of the applicator. The puncture protrusion is configured to puncture an end surface of a cartridge within the internal chamber, which cartridge contains a liquid that is resultantly allowed to flow through a passageway in the puncture protrusion toward an applicator pad for application onto a surface. Puncturing is achieved in response to rotation of an advancer including a pinion portion that tangentially engages a surface of the cartridge, which rotation is translated to longitudinal advancement of the cartridge toward the puncture protrusion.

21 Claims, 7 Drawing Sheets

METHOD AND APPARATUS FOR AN APPLICATOR

TECHNICAL FIELD

These teachings relate generally to applicators, and more specifically to applicators for applying liquids.

BACKGROUND

Applicators are commonly used to apply liquid or gels to various surfaces. For example, in a surgical setting, an applicator may be used to apply a surgical preparation agent, such as Chlorhexidine Gluconate ("CHG"), to a patient's skin in preparation for surgery. An applicator may be equipped with a scrub brush and a mechanism to disperse or dispense the liquid onto the skin either directly or through the applicator. Various applicators may include or be configured to operate with a vial or cartridge of liquid that can be activated to allow the liquid to be dispensed onto the patient. Various ways of activating the cartridge and allowing dispersion of the liquid are presently known. For example, prior art solutions include breaking a frangible vial to release the liquid therein such that it can then be dispersed onto the patient.

Though suitable for at least some purposes, such approaches do not necessarily meet all needs of all application settings and/or all users. For example, the pressure required to break a frangible vial may be greater than certain users are capable of producing. Further, such a process often requires both hands. Additionally, such solutions may be relatively inefficient in terms of liquid dispersion as, depending on the location of a break, significant amounts of the liquid may remain in unbroken portions of the vial and broken shards of the frangible vial may actually inhibit flowing of the liquid. Further still, such solutions may fail to communicate to a user that the vial or cartridge is fully or optimally activated.

BRIEF DESCRIPTION OF THE DRAWINGS

The above needs are at least partially met through provision of the applicator described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a device is provided including a handle, which further includes an applicator pad coupler and an internal chamber. A puncture protrusion is disposed on an inner surface at one end of the internal chamber and has a passageway extending therethrough between the internal chamber and the applicator pad coupler. The puncture protrusion is configured to puncture an end surface of a cartridge within the internal chamber and to allow liquid to flow from the cartridge to the applicator pad coupler. The device also includes an advancer which includes a pinion portion that tangentially engages a surface of the cartridge. The pinion portion rotates about a rotation axis to advance the cartridge toward the puncture protrusion along a longitudinal axis of the internal chamber through the tangential engagement between the pinion portion and the cartridge.

So configured, a cartridge containing a liquid solution (such as CHG, iodine, etc.) will remain sealed until such time as the solution is needed, for example, to prepare a patient for surgery. To use the applicator, a user can easily activate the cartridge (e.g., by puncturing or breaking the cartridge or otherwise allowing liquid to exit the cartridge) to allow the liquid to be applied to the patient. Activation can be achieved with one hand rather than two as may be needed by other prior art approaches. Further, given the location of the puncture protrusion in relation to the cartridge, the cartridge is capable of being completely or nearly completely emptied of the liquid therein, thus resulting in an efficient approach to prevent wasted solution.

Figure 1:
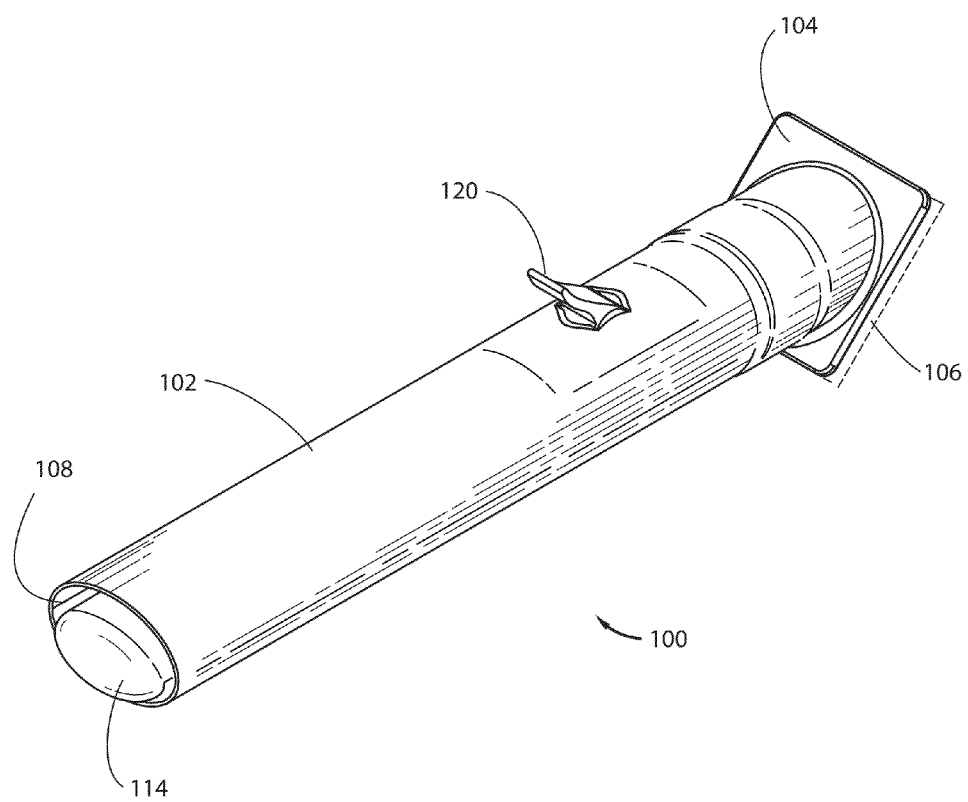
FIG. 1 is a perspective view of an applicator as configured in accordance with various embodiments of these teachings.

These and other benefits may become clearer upon making a thorough review and study of the following detailed description. Referring now to the drawings, and in particular to FIG. 1, an illustrative applicator compatible with many of these teachings will now be presented.

The applicator 100 includes a handle 102 with an exterior surface, which handle 102 includes or is attached to an applicator pad coupler 104 configured to physically couple to an applicator pad 106 (such as a sponge, brush, or other porous pad). The applicator pad 106 may be coupled to the applicator pad coupler 104 by an adhesive, one or more clips, by being slid onto the applicator pad coupler 104 or by other common means. The handle 102 also includes an internal chamber 108. The handle 102 and the internal chamber 108 each have a longitudinal axis, which axes correspond to each other (i.e., are the same axis and hence coaxial or are at least parallel to each other). The internal chamber 108 may have an oval cross section (as shown) or, by other approaches, a circular, square, or rectangular cross section or a cross section of another shape. The oval cross section allows for a cartridge 114 to be inserted in one of two orientations, which orientation is maintained as the cartridge 114 is not allowed to rotate significantly within the internal chamber 108 (for example, while it may be possible for the cartridge 114 to rotate, say, 1 to 3 degrees, the cartridge 114 cannot rotate beyond that limited range).

The end of the handle 102 may be open (as depicted), or may alternatively be closed by a cap or other means of sealing. In some approaches, an o-ring or other seal may be provided between the exterior surface of the cartridge 114 and an interior surface of the internal chamber 108 to prevent liquid from escaping out the end of the handle 102 and to provide stability. The applicator 100 may be made of a rigid plastic (such as polypropylene or polyethylene, though other plastics are possible), metal, glass, or another suitable rigid material. The applicator 100 may be assembled, sterilized, packaged, and made available with the cartridge 114 installed therein. In another approach, the applicator 100 may be made available separate from the cartridge 114, wherein the cartridge 114 can be inserted into the applicator 100 in the field at the time of use.

Figure 2:
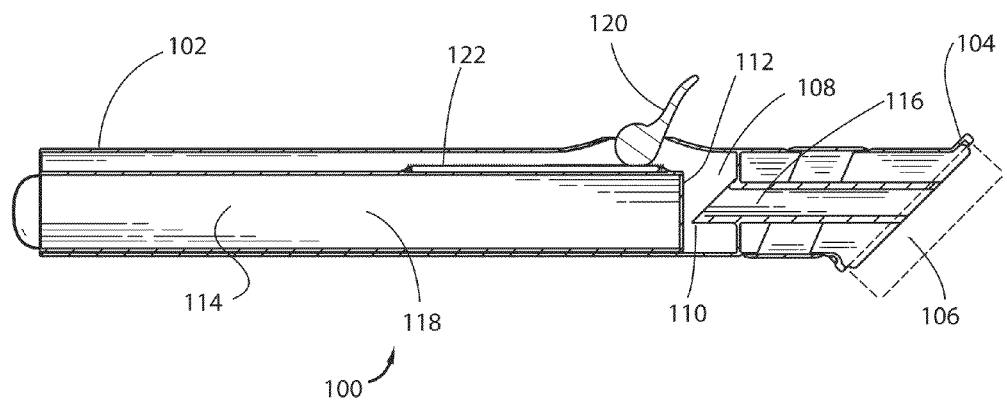
FIG. 2 is a cross-sectional view of an applicator as configured in accordance with various embodiments of these teachings.

Referring now to FIG. 2, a cross sectional view of the applicator 100 is provided. The applicator 100 also includes a puncture protrusion 110 disposed on an inner surface at a first end portion of the internal chamber 108. As is shown in FIG. 2, the puncture protrusion 110 is disposed on an the end surface of the internal chamber 108 at the end of the internal chamber 108 that is closest to the applicator pad coupler 104, though other configurations are possible. The puncture protrusion 110 is configured to puncture an end surface 112 of a cartridge 114 within the internal chamber 108. For example, the puncture protrusion 110 can be shaped to have an angled or pointed portion well suited to puncture the end surface 112 of the cartridge 114. The puncture protrusion 110 includes a passageway 116 extending therethrough between the internal chamber 108 and the applicator pad coupler 104. The passageway 116 allows liquid 118 to flow from the cartridge 114 to the applicator pad coupler 104 when the puncture protrusion 110 punctures the end surface 112 of the cartridge 114.

Figure 3:
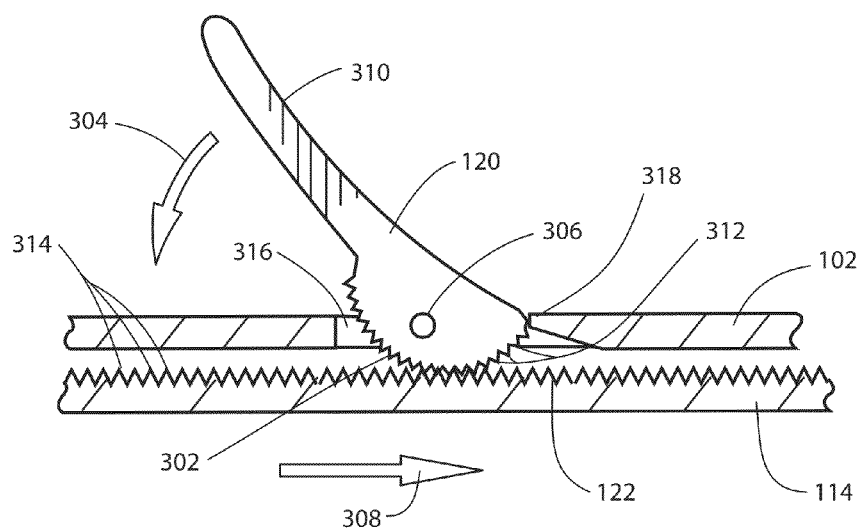
FIG. 3 is a detail image of an advancer that might be found on the applicator of FIG. 1, as configured in accordance with various embodiments of these teachings.

The applicator 100, and more specifically the handle 102, also includes an advancer 120. Referring now to FIG. 3, an expanded detail view of the advancer 120 is provided in accordance with at least one approach. The advancer 120 is rotatably coupled to the handle 102 and includes a pinion portion 302 that protrudes into the internal chamber 108 and is configured to tangentially engage an engagement surface 122 or sidewall of the cartridge 114. The advancer 120, and more specifically the pinion portion 302, is also configured to rotate 304 about a rotation axis 306 to thereby advance 308 the cartridge 114 toward the puncture protrusion 110 through the tangential engagement between the pinion portion 302 and the engagement surface 122. By one approach, the cartridge 114 will only need to advance 308 approximately ¼ of an inch for the puncture protrusion 110 to puncture the end surface 112. However, with other configurations, that distance may be less or more, and is also dependent upon how far from the puncture protrusion 110 the end surface 112 is situated at the onset of the advancement 308.

By one approach, and as is shown in FIGS. 1-3, the advancer includes a lever portion 310 which rotates 304 about the rotation axis 306 in tandem with the pinion portion 302. For example, the pinion portion 302 may rotate 304 about the rotation axis 306 in response to rotation 304 of the lever portion 310. The lever portion 310 is accessible along the exterior surface of the handle 102, which is external to the internal chamber 108. The lever portion 310 also provides leverage to a user to advance 308 the cartridge 114, which can help enable a user to activate the cartridge 114 with a single hand using a thumb or a finger.

As shown in FIG. 3, the pinion portion 302 may be an arc portion (a segment of a larger circle), which arc portion may be concentric with the axis of rotation 306, or which may be offset therefrom to provide a camming action as it rotates 304 about the axis of rotation 306. The lever portion 310 may extend generally outwardly from the axis of rotation 306, from a center of the arc portion, or from some other point. Alternatively, and as is shown in FIG. 2, the pinion portion 302 may include a complete or near complete circle. In such an approach, the lever portion 310 may extend generally tangential from an outer circular edge of the pinion portion 302 to allow for the lever portion 310 to remain closer to the exterior surface of the handle 102 after the advancer 120 has been rotated to advance the cartridge 114. This helps prevent the lever portion 310 from accidentally being rotated in the opposite direction to uncouple the cartridge 114 from the puncture protrusion 110 after the cartridge 114 has been activated.

In some embodiments, the pinion portion 302 includes a plurality of teeth 312 such that it resembles a gear. The teeth 312 may interface with a plurality of teeth 314 on the cartridge 114 that may comprise the engagement surface 122 of the cartridge 114. Alternatively, the teeth 312 on the pinion portion 302 may interface with an engagement surface 122 that does not include teeth 314 and may instead comprise a rough or textured surface (such as a rough molded surface, a sputtered texture, or the like) or an unaltered exterior surface of the cartridge 114.

With continued reference to FIG. 3, the handle 102 may include an advancer opening 316 that receives and rotatably couples the advancer 120 to the handle 102. Such coupling may include indentations or openings in sidewalls of the advancer opening 316 that receive and/or capture ends or portions of an axle member of the advancer 120 or ends or portions of axle protrusions disposed on the sides of the advancer 120 at the rotation axis 306. Conversely, indentations or openings in the advancer 120 may couple the advancer 120 to the handle 102 by receiving and/or capturing axle protrusions disposed on the sides of the advancer opening 316. In one form, the advancer opening 316 may include a tab 318 that is configured to engage the pinion portion 302 or another portion of the advancer 120. If the pinion portion 302 includes a plurality of teeth 312, when the advancer 120 is rotated 304 the tab 318 may bend slightly upward and wedge between individual teeth to ratchet the advancer 120 to hold it or prevent it from rotating in the opposite direction. Thus, rotation 304 in only one direction about the rotation axis 306 may be allowed. The tab 318 may be tapered in thickness or width to allow it to bend more easily. Further, the interaction of the tab 318 and the plurality of teeth 312 while it is rotated 304 will provide an audible and tactile response (e.g., a series of clicks) to indicate to a user that the advancer 120 is indeed being rotated.

Figure 4:
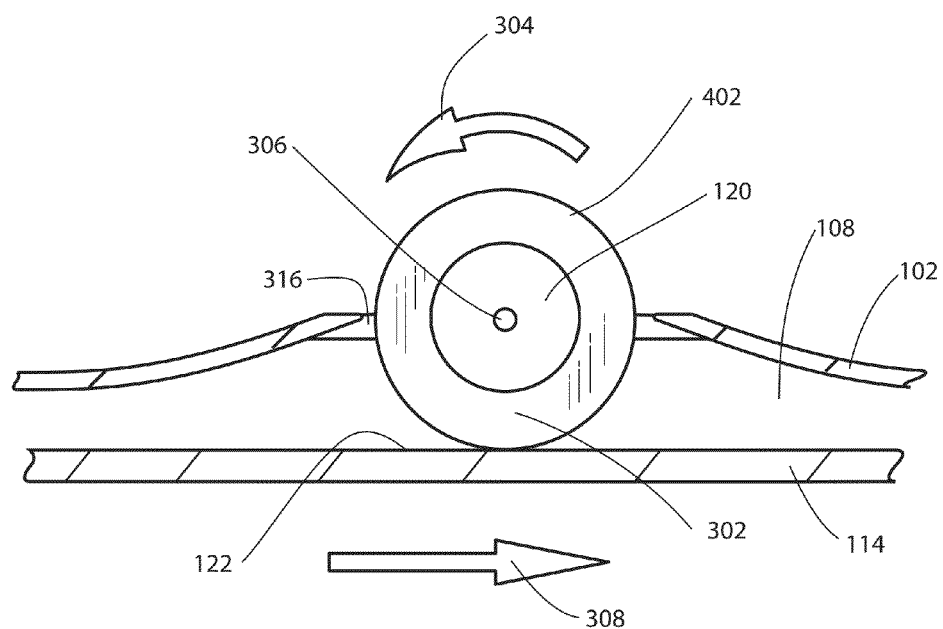
FIG. 4 is a detail image of another advancer that might be found on the applicator of FIG. 1, as configured in accordance with various embodiments of these teachings.

Turning now to FIG. 4, by another approach the advancer 120 may omit the lever portion 310 and may instead include a roller wheel portion 402. The roller wheel portion 402 rotates about the rotation axis 306 in tandem with the pinion portion 302. Like the lever portion 310, the roller wheel portion 402 is accessible along the exterior surface of the handle 102, which is external to the internal chamber 108, so that the roller wheel portion 402 can be rotated 304 by a thumb or a finger. By one approach, the pinion portion 302 and roller wheel portion 402 are distinguishable portions of the advancer 120. They may be distinguishable by having distinct radiuses about the rotation axis 306 and/or different finishes. For example, the roller wheel portion 402 may include a grippy exterior surface or coating (for example, being rubber, rubber-like, or of a grippy plastic) for providing relatively-increased grip while interfacing with a finger while the pinion portion 302 may include a plurality of teeth 312 for interfacing with the cartridge 114 (as shown in FIG. 3).

In another form, the pinion portion 302 comprises the roller wheel portion 402 so that they are physically indistinguishable. In such an approach, the advancer 120 is a circular disc or cylinder that is concentric with the rotation axis 306. In this approach, the advancer 120 may include a uniform finish, for example, a plurality of teeth 312 that continue all the way around the circular advancer 120 (which may resemble a complete pinion gear) or a uniform grippy surface or coating. Such a grippy surface or coating allows for improved grip between the advancer 120 and a finger and between the advancer 120 and the engagement surface 122 of the cartridge 114.

Further, it should be noted that these teachings with respect to the grippy surface or coating can equally apply to the levered advancer embodiment described in FIGS. 2 and 3, both with respect to the lever portion 310 and the pinion portion 302. Further, such a grippy surface, coating, or construction is usable with the tab 318 as described with respect to FIG. 3, both in a levered configuration and in the roller wheel configuration of FIG. 4. In such a configuration, the tab 318 may simply dig into the grippy surface or coating and prevent or oppose rotation in the opposite direction.

With continued reference to FIG. 4, the portion of the handle 102 surrounding the advancer opening 316 may be raised in relation to the remainder of the exterior surface of the handle 102. By raising this surface, the distance between the rotation axis 306 and the engagement surface 122 of the cartridge 114 can be increased, which allows for a larger radius pinion portion 302 and/or roller wheel portion 402. The larger radius, in turn, allows for increased surface area of the advancer 120 that is accessible by a finger along the exterior surface of the handle 102 and allows for an increased surface area of the pinion portion 302 to engage the engagement surface 122 of the cartridge 114. These teachings are equally applicable to the levered embodiment of FIG. 3. Particularly, if the area around the advancer opening 316 is raised, resulting in increased radius of the pinion portion 302, the cartridge 114 can be linearly advanced 308 further per degree of rotation 304 of the advancer 120 than compared to a pinion portion 302 with a smaller radius.

Figure 5:
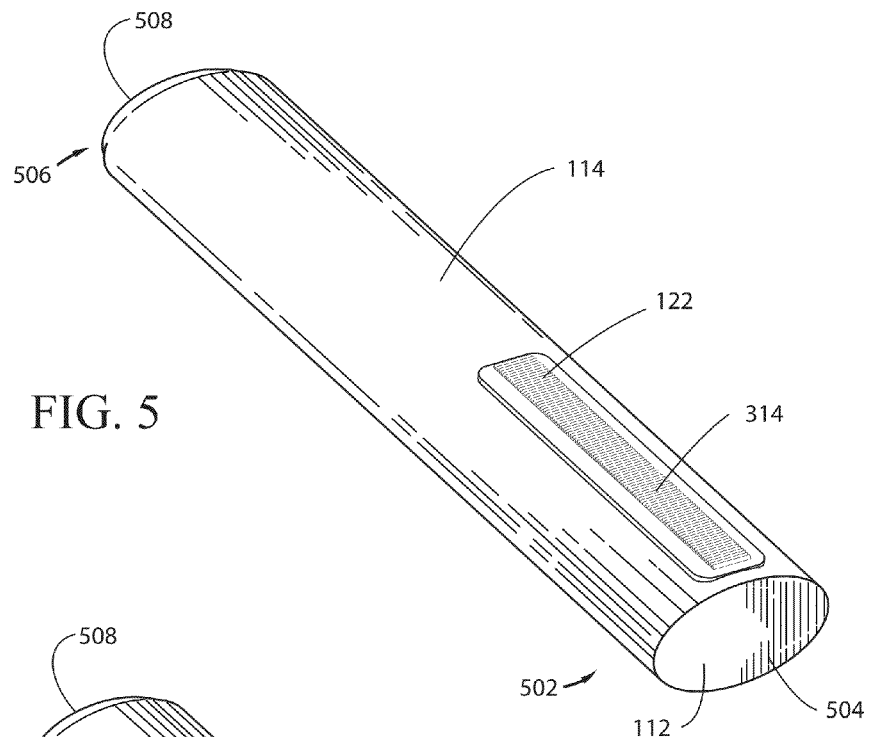
FIG. 5 is a perspective view of an example cartridge that might be used with the applicator of FIG. 1, as configured in accordance with various embodiments of these teachings.
Figure 6:
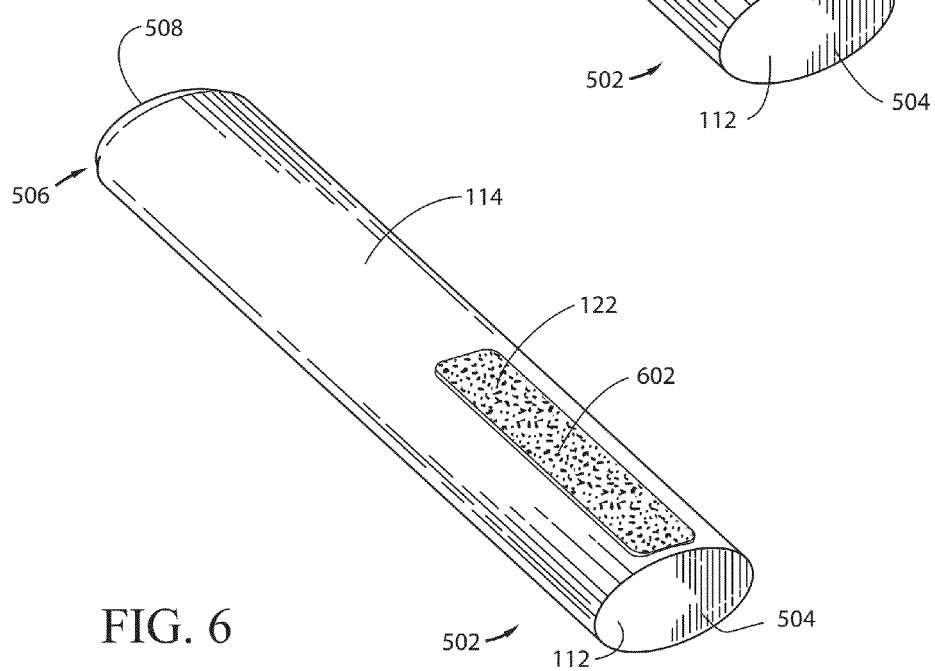
FIG. 6 is a perspective view of another example cartridge that might be used with the applicator of FIG. 1, as configured in accordance with various embodiments of these teachings.

Turning now to FIGS. 5 and 6, example cartridges 114 are shown in accordance with various approaches. As mentioned above, the cartridge 114 may have an oval cross section as shown, though other cross section shapes are possible. The cartridge 114 may be made of a rigid plastic (such as polypropylene or polyethylene, though other plastics are possible), metal, glass, or another suitable rigid material. A plastic construction is favored, however, due to its ability to be easily molded and its low cost. At a first end 502, the cartridge 114 may have an opening (not shown). The opening allows the cartridge to be filled with the liquid 118, which opening is then sealed to create a sealed cartridge 114. Such a seal may be, for example, a foil seal 504 that forms the end surface 112 to be punctured by the puncture protrusion 110. Other sealing approaches are possible, including a thin plastic, gel, wax, or the like. An engagement surface 122 may be disposed on a top surface of the cartridge. Optionally, the engagement surface 122 may be integrated with the cartridge 114 itself through a single molding process. As is shown in FIG. 5, the engagement surface 122 may include a plurality of teeth 314 to interact with the pinion portion 302 of the advancer 120. Alternatively, as is shown in FIG. 6, the engagement surface 122 may instead include a rough or textured surface 602. The rough or textured surface 602 may be a rough molded surface, a sputtered texture added to the engagement surface 122, a grippy surface, or the like. The rough surface 602 provides additional grip for the interaction with the pinion portion 302 of the advancer 120.

As is shown in FIGS. 5 and 6, the engagement surface 122 may include portions that are raised to make the surface relatively flat as compared to a curved exterior surface of the cartridge 114. Alternatively, the plurality of teeth 314 (FIG. 5) or the rough or textured surface (FIG. 6) may be disposed on a curving surface of the cartridge 114. Alternatively still, the engagement surface 122 may be an unaltered exterior surface of the cartridge 114, lacking teeth or texture beyond the normal texture of the exterior surface of the cartridge 114.

Figure 7:
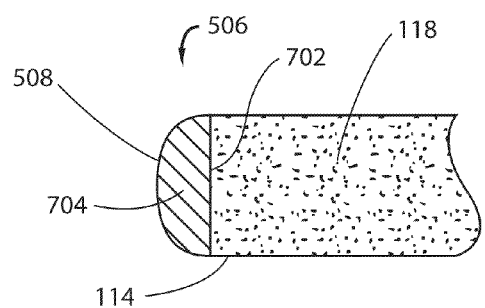
FIG. 7 is a detail cross-sectional view of a portion of the cartridges of FIGS. 5 and 6, as configured in accordance with various embodiments of these teachings.

Turning now to FIG. 7, by one approach the second end 506 of the cartridge 114, when inserted into the internal chamber 108 of the handle 102, will be accessible outside of the end of the handle 102. Such access may be direct or indirect (e.g., through an actuator). The end surface 508 may be rounded and flexible so as to be depressible to comprise an actuator. Within the second end 506, a thin barrier 702 may exist to separate the liquid 118 from a relatively small amount of highly-potent dye 704. The thin barrier 702 is configured to rupture in response to actuation (depression) of the end surface 508 (actuator) to allow the dye 704 to color the liquid 118. This allows the liquid 118 to be more readily visible to the unaided human eye when being applied to a patient during surgical preparation.

Figure 8:
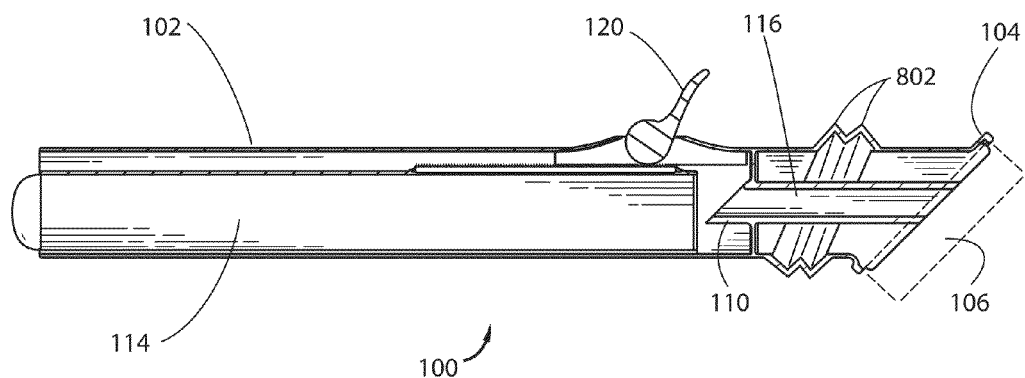
FIG. 8 is a side cross-sectional view of an alternative applicator as configured in accordance with various embodiments of these teachings.

Turning now to FIG. 8, an applicator 100 is shown in accordance with various alternate approaches. The applicator 100 may include a pivotable applicator pad coupler 104 that allows the applicator pad coupler 104 (and thus the applicator pad 106) to pivot in relation to the handle 102. This can better account for variations in the contours of surfaces to which the liquid is being applied. To effect the pivoting, the applicator may include one or more flexible accordion bends (or folds) 802 circling a portion of the handle 102, though other means are contemplated. The passageway 116 through the puncture protrusion 110 may be formed, at least in part, of a flexible material such as flexible tubing.

Figure 9:
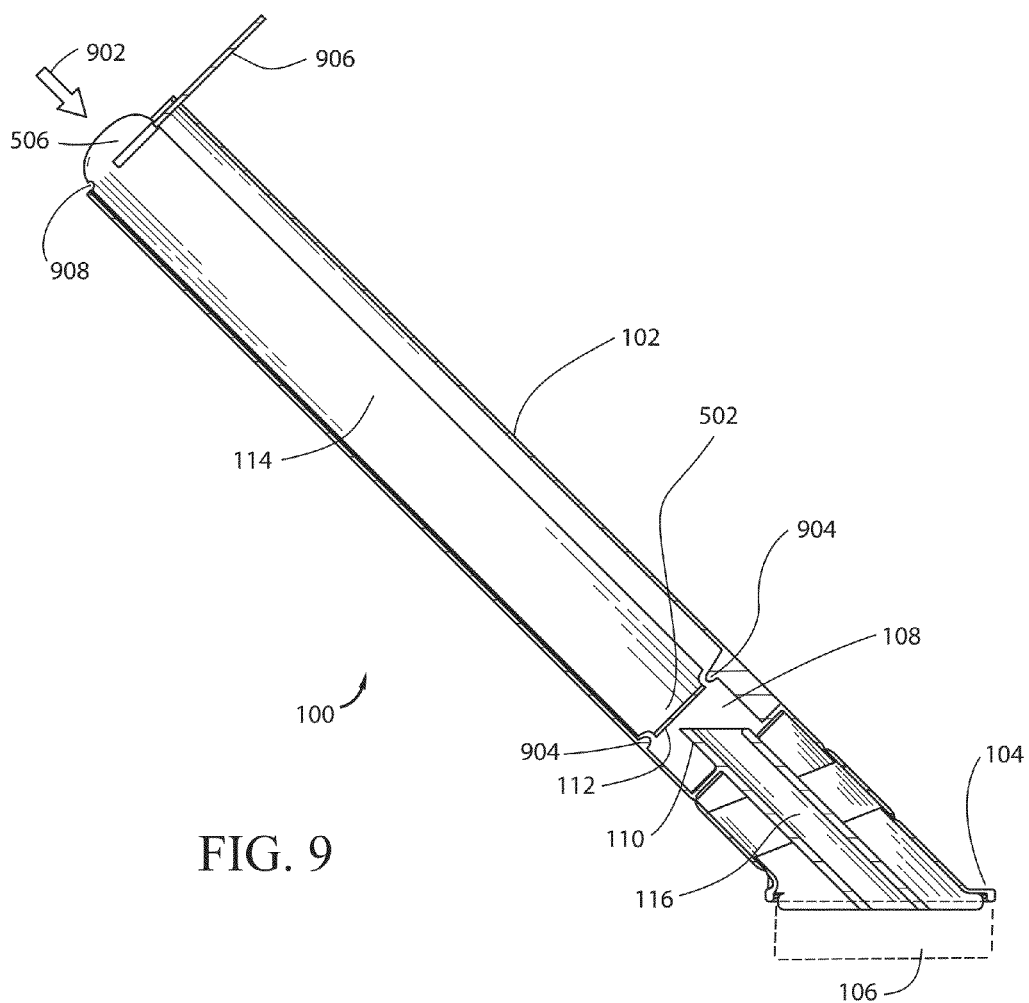
FIG. 9 is a side cross-sectional view of another alternative applicator as configured in accordance with various embodiments of these teachings.

With reference now to FIG. 9, an applicator 100 is shown including alternate structure to activate the cartridge 114. In this approach, the second end 506 of the cartridge 114 is pushed 902 into the internal chamber 108 toward the puncture protrusion 110. Near the puncture protrusion 110, the internal chamber 108 includes one or more nubs 904. The nubs 904 may be a single ridge that circles the inside surface of the internal chamber 108 or a series of multiple individual nubs 904. The nubs 904 may be molded into the surface of the interior chamber, or may be attached thereto. The nubs 904 act as a pre-stop to prevent the cartridge 114 from advancing toward the puncture protrusion without exertion of force 902 by the user. When a force pushes 902 the end 506 of the cartridge 114 in, and that force is greater than a force required to move the first end 502 of the cartridge 114 past the nubs 904, then the cartridge 114 will advance toward the puncture protrusion 110 and the end surface 112 of the cartridge will be punctured, allowing the liquid to flow through the passageway 116 to the applicator pad 106.

Additionally, in some approaches, the applicator 100 will include a safety 906 to prevent the cartridge 114 from being unintentionally pushed in 902. The safety 906 may include a plastic clip or ring that possibly corresponds with a groove 908 in the second end 506 of the cartridge. With a clip-type safety 906 engaging the groove 908, interference between the safety 906 and the end of the handle 102 prevents the cartridge 114 from being pushed in 902. When the safety 906 is removed, the cartridge 114 may then be pushed in 902. It is noted that various elements of the approach just described may be utilized with other approaches described elsewhere herein. For example, the nubs 904 or the safety 906 may be also incorporated with approaches that utilize the advancer 120, or with other approaches described hereafter.

Figure 10:
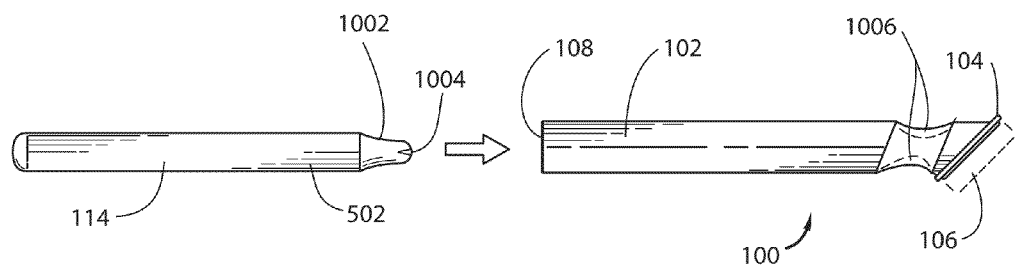
FIG. 10 is a side cross-sectional view of another alternative applicator as configured in accordance with various embodiments of these teachings.

In another form, as is illustrated in FIG. 10, the cartridge 114 includes a bite-valve 1002 at the first end 502. The bite-valve 1002 may be formed of silicone, rubber, or other resilient material capable of being deformed through depressions while returning to its previous form when the depressions cease. The bite-valve 1002 may include one or more linear slits 1004 at the end that deform to create an opening when force is exerted on the bite-valve 1002 from the sides. The cartridge 114 is inserted into the handle 102, which handle includes one or more bite-valve actuators 1006 on the exterior of the handle corresponding to the location where the bite-valve 1002 resides when inserted. When the bite-valve actuators 1006 are actuated by depressing the actuators 1006 in toward the internal chamber 108 of the handle 102, the actuators 1006 create pressure on the sides of the bite-valve 1002 to deform the bite-valve 1002, which in turn opens the slits 1004 to allow liquid 118 therein to flow through a passageway toward the applicator pad 106. When the actuators 1006 are released, the bite-valve 1002 returns to its closed state, disallowing the liquid from flowing.

Figure 11:
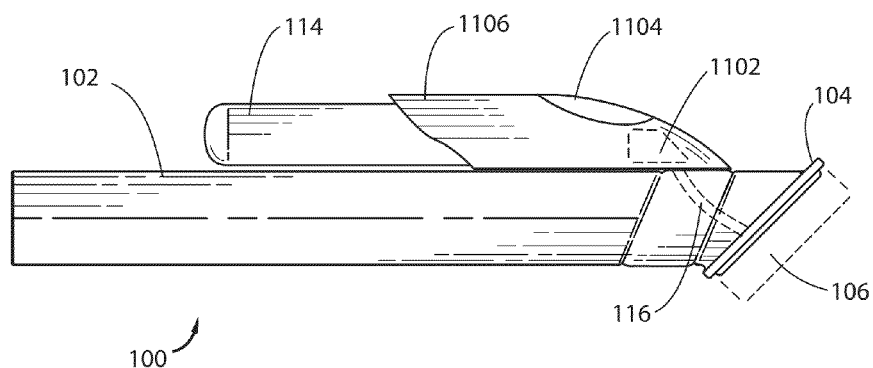
FIG. 11 is a side cross-sectional view of another alternative applicator as configured in accordance with various embodiments of these teachings.

By other approaches, and as illustrated in FIG. 11, the handle 102 includes a pump 1102 or valve that may be battery operated and may operate in response to depression of a button or actuator 1104. The pump 1102 may reside within the internal chamber 108, or as shown in FIG. 11, may reside in an external housing 1106. The external housing 1106 may be configured to receive the cartridge 114 and may include the button or actuator 1104 on an external surface thereof. When the actuator 1104 is actuated, the pump 1102 will withdraw liquid from the cartridge 114 and send it to the applicator pad 106 through passageway 116. This provides a system to nearly effortlessly (in terms of human effort) deliver solution to the applicator pad 106 when needed.

One or more methods corresponding to the above described applicator 100 are also contemplated. In one approach, a method includes rotating 304 an advancer 120 about a rotation axis 306, the advancer 120 including a pinion portion 302 tangentially engaging a sidewall portion of the cartridge 114 to thereby advance 308 the cartridge 114 along a longitudinal axis of the internal chamber 118. The method also includes responsively puncturing the end surface 112 of the cartridge 114 by the puncture protrusion 110 disposed on an inner surface of the internal chamber 108 at one end portion, thereby enabling a liquid 118 to flow from the cartridge 114 to an applicator pad 106 via the passageway 116.

In varying approaches, the method may also include (in lieu of the foregoing or in combination therewith) rotating the advancer 120 in response to rotating a lever portion 310 of the advancer 120 about the rotation axis 306. By another approach, the method further includes a plurality of teeth 312 of the pinion portion 302 interfacing with the plurality of teeth 314 of a sidewall portion of the cartridge 114. The method might also include ratcheting the advancer 120 such that it can only rotate in one direction. By yet another approach, the method also includes dying the liquid 118 of the cartridge 114 by rupturing a thin barrier 702 between the liquid 118 and a dye 704.

So configured, a cartridge containing a liquid solution (such as CHG, iodine, etc.) will remain sealed until such time as the solution is needed, for example, to prepare a patient for surgery. To use the applicator, a user can easily activate the cartridge (e.g., by puncturing or breaking the cartridge or otherwise allowing liquid to exit the cartridge) to allow the liquid to be applied to the patient. Activation can be achieved with one hand rather than two as may be needed in other approaches. Further, given the location of the puncture protrusion in relation to the cartridge, the cartridge is capable of being completely or nearly completely emptied of the liquid therein, thus resulting in less wasted solution.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A device comprising:
   a handle having a longitudinal axis, the handle further comprising:
   an applicator pad coupler;
   an internal chamber having a longitudinal axis corresponding to the longitudinal axis of the handle;
   a puncture protrusion disposed on an inner surface at a first end portion of the internal chamber, the puncture protrusion configured to puncture an end surface of a cartridge within the internal chamber, the puncture protrusion having a passageway extending therethrough between the internal chamber and the applicator pad coupler to allow liquid to flow from the cartridge to the applicator pad coupler when the puncture protrusion punctures an end surface of the cartridge; and
   an advancer comprising a pinion portion, the pinion portion configured to tangentially engage a surface of the cartridge within the internal chamber;
   wherein the pinion portion of the advancer is configured to rotate about a rotation axis to advance the cartridge through tangential engagement therewith along the longitudinal axis of the internal chamber toward the puncture protrusion.

2. The device of claim 1 wherein the advancer further comprises a lever portion configured to rotate about the rotation axis in tandem with the pinion portion, wherein the lever portion is accessible external to the internal chamber.

3. The device of claim 1 wherein the advancer further comprises a roller wheel portion configured to rotate about the rotation axis in tandem with the pinion portion, wherein the roller wheel portion is accessible external to the internal chamber.

4. The device of claim 3 wherein the pinion portion comprises the roller wheel portion, and wherein the advancer comprises at least one of a circular disc and a cylinder that is disposed concentrically with the rotation axis.

5. The device of claim 1 further comprising the cartridge.

6. The device of claim 5, wherein the cartridge comprises an engagement surface disposed on an exterior surface thereof, the engagement surface configured to tangentially engage the pinion portion of the advancer.

7. The device of claim 5 wherein the end surface of the cartridge comprises a foil seal configured to be punctured by the puncture protrusion.

8. The device of claim 1 wherein the pinion portion comprises a plurality of teeth configured to interface with a plurality of teeth of the cartridge.

9. The device of claim 1 wherein the handle comprises an advancer opening configured to receive and rotatably couple the advancer to the handle, the advancer opening further comprising at least one tab configured to ratchet the advancer to allow rotational movement about the rotation axis in only one direction.

10. A method comprising:
at a handle of an applicator, the handle comprising an internal chamber having a cartridge at least partially disposed therein:
rotating an advancer about a rotation axis, the advancer comprising a pinion portion tangentially engaging a sidewall portion of the cartridge to thereby advance the cartridge along a longitudinal axis of the internal chamber;
puncturing an end surface of the cartridge by a puncture protrusion disposed on an inner surface of the internal chamber at one end portion of the internal chamber, the puncturing occurring in response to advancing the cartridge and thereby enabling a liquid to flow from the cartridge to an applicator pad via a passageway running through the puncture protrusion and extending between the internal chamber and the applicator pad.

11. The method of claim 10 wherein rotating the advancer is in response to rotating a lever portion of the advancer about the rotation axis, the lever portion being accessible external to the internal chamber.

12. The method of claim 10 wherein puncturing the end surface of the cartridge by the puncture protrusion further comprises puncturing a foil seal on the end surface of the cartridge.

13. The method of claim 10 further comprising a plurality of teeth of the pinion portion interfacing with a plurality of teeth of the sidewall portion of the cartridge.

14. The method of claim 10 further comprising ratcheting the advancer such that the advancer can only rotate in one direction about the rotation axis.

15. The method of claim 10 further comprising dying the liquid of the cartridge by rupturing a thin barrier between the liquid of the cartridge and a dye.

16. A device comprising:
an applicator pad;
a handle comprising an exterior surface and an internal chamber, the internal chamber comprising a longitudinal axis;
a cartridge housed at least partially within the internal chamber;
an advancer rotatably coupled to the handle, a pinion portion of the advancer protruding into the internal chamber and tangentially engaging a sidewall of the cartridge, at least another portion of the advancer accessible along the exterior surface of the handle, wherein the advancer is configured to rotate about a rotation axis and, through tangential engagement with the cartridge, advance the cartridge along the longitudinal axis of the internal chamber toward one end portion of the internal chamber; and
a puncture protrusion disposed on a surface of the internal chamber at the one end portion of the internal chamber, the puncture protrusion having a passageway extending therethrough between the internal chamber and the applicator pad, the puncture protrusion configured to puncture an end surface of the cartridge in response to the cartridge being advanced by the advancer toward the one end portion and to responsively allow a liquid within the cartridge to flow through the passageway to the applicator pad.

17. The device of claim 16 wherein the at least another portion of the advancer accessible along the exterior surface of the handle further comprises a lever portion of the advancer, the lever portion configured to rotate in tandem with the pinion portion about the rotation axis.

18. The device of claim 16 wherein the at least another portion of the advancer accessible along the exterior surface of the handle further comprises a roller wheel portion of the advancer, the roller wheel portion configured to rotate in tandem with the pinion portion about the rotation axis.

19. The device of claim 16 wherein the end surface of the cartridge further comprises a foil seal.

20. The device of claim 16 wherein the pinion portion comprises a plurality of teeth configured to interface with a plurality of teeth of the cartridge.

21. The device of claim 16 wherein the cartridge further comprises a dye and a thin barrier separating the dye from the liquid within the cartridge, the thin barrier configured to rupture in response to actuation of an actuator of the cartridge.

* * * * *